US011801354B2

(12) United States Patent
Monsalud et al.

(10) Patent No.: US 11,801,354 B2
(45) **Date of Patent: *Oct. 31, 2023**

(54) AEROSOL DELIVERY DEVICE WITH CONDUCTIVE INSERTS

(71) Applicant: RAI Strategic Holdings, Inc., Winston-Salem, NC (US)

(72) Inventors: Luis Monsalud, Kernersville, NC (US); Andries Sebastian, Clemmons, NC (US); Stephen B. Sears, Siler City, NC (US); John-Paul Mua, Advance, NC (US); Vahid Hejazi, Winston-Salem, NC (US); Rajesh Sur, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 11 days.

This patent is subject to a terminal disclaimer.

(21) Appl. No.: 17/569,146

(22) Filed: Jan. 5, 2022

(65) Prior Publication Data

US 2022/0126038 A1 Apr. 28, 2022

Related U.S. Application Data

(63) Continuation of application No. 16/142,558, filed on Sep. 26, 2018, now Pat. No. 11,247,005.

(51) Int. Cl.
*A61M 15/06* (2006.01)
*A24B 3/14* (2006.01)
(Continued)

(52) U.S. Cl.
CPC ............... *A61M 15/06* (2013.01); *A24B 3/14* (2013.01); *A24B 13/02* (2013.01); *A24D 1/002* (2013.01);
(Continued)

(58) Field of Classification Search
CPC ............ A61M 15/0041; A61M 11/042; A61M 15/06; A61M 15/0035; A61M 15/0003;
(Continued)

(56) References Cited

U.S. PATENT DOCUMENTS 2,057,353 A * 10/1936 Whittemore, Jr. ............ 392/404
2,104,266 A * 1/1938 McCormick .......... A24F 40/485
131/330

(Continued)

FOREIGN PATENT DOCUMENTS

CN 1541577 11/2004
CN 2719043 8/2005

(Continued)

OTHER PUBLICATIONS

International Search Report from corresponding International Application No. PCT/IB2019/058183, dated Nov. 15, 2019.

*Primary Examiner* — Eric S Stapleton
(74) *Attorney, Agent, or Firm* — WOMBLE BOND DICKINSON (US) LLP

(57) ABSTRACT

The present disclosure provides aerosol delivery devices. In an example implementation, an aerosol delivery device comprises an aerosol source member that defines an outer surface and an interior area and includes a substrate material having an aerosol precursor composition associated therewith, a control body having a housing that is configured to receive the aerosol source member, an electrical energy source coupled with the housing, and a heating assembly operatively connected to the electrical energy source. The heating assembly includes a plurality of spikes that may be configured to articulate between a retracted position, in which the plurality of spikes is not in contact with the aerosol source member, and a heating position, in which the plurality of spikes pierces through the outer surface of the (Continued)

substrate material and into a portion of the interior area thereof.

20 Claims, 8 Drawing Sheets

(51) Int. Cl.
*A24B 13/02* (2006.01)
*A24D 1/00* (2020.01)
*A24D 1/14* (2006.01)
*A61M 11/04* (2006.01)
*H05B 3/46* (2006.01)

(52) U.S. Cl.
CPC ............. *A24D 1/14* (2013.01); *A61M 11/042* (2014.02); *H05B 3/46* (2013.01); *A61M 2205/3653* (2013.01)

(58) Field of Classification Search
CPC .... A61M 2016/0021; A61M 2205/584; A61M 2016/0036; A61M 2205/3368; A61M 2205/581; A61M 2205/8243; A61M 2205/8206; A61M 2205/582; A61M 2205/13; A61M 2016/0024; A61M 2205/3653; A24D 1/002; A24D 1/20; A24D 1/14; H05B 3/46; A24B 13/02; A24B 3/14; A24F 40/46; A24F 40/20
USPC ........................................................ 392/404
See application file for complete search history.

(56) References Cited

U.S. PATENT DOCUMENTS 3,200,819 A * 8/1965 Gilbert .................. A24F 40/485 131/273
4,735,217 A * 4/1988 Gerth ...................... A24F 40/50 131/273
4,922,901 A * 5/1990 Brooks ............... A61M 16/109 131/273
5,042,510 A * 8/1991 Curtiss .................... A24F 42/20 131/272
5,060,671 A * 10/1991 Counts .................... A24F 40/30 131/273
5,093,894 A * 3/1992 Deevi ..................... A24F 40/46 392/404
5,159,940 A * 11/1992 Hayward ................. A24D 1/22 131/365
5,261,424 A * 11/1993 Sprinkel, Jr. ........... A24F 40/51 392/386
5,388,574 A * 2/1995 Ingebrethsen .... A61M 15/0085 128/203.26
5,530,225 A * 6/1996 Hajaligol ................ A24F 40/46 131/194
5,591,368 A * 1/1997 Fleischhauer ........... A24F 40/46 131/194
5,687,746 A * 11/1997 Rose ..................... A61M 15/00 131/273
5,726,421 A * 3/1998 Fleischhauer ........... A24F 40/40 131/194
5,865,185 A * 2/1999 Collins .................... A24D 3/17 131/194
5,894,841 A * 4/1999 Voges ................... A61M 15/06 128/200.14
6,089,857 A * 7/2000 Matsuura .............. A61M 15/06 431/153
6,125,853 A * 10/2000 Susa ....................... A24F 40/46 131/194
6,155,268 A * 12/2000 Takeuchi .............. A24F 40/485 131/194
6,164,287 A * 12/2000 White ..................... A24F 42/10 131/194
6,196,218 B1 * 3/2001 Voges ................. B05B 17/0607 128/200.14
6,598,607 B2 * 7/2003 Adiga ..................... A24F 42/10 131/194
6,601,776 B1 * 8/2003 Oljaca ..................... B05B 17/04 977/869
6,854,470 B1 * 2/2005 Pu .......................... A24F 42/20 131/276
6,890,624 B1 * 5/2005 Kambe .................. B82Y 30/00 427/205
7,117,867 B2 * 10/2006 Cox ..................... A61M 11/042 128/200.14
7,423,512 B1 * 9/2008 Reitz ...................... C09K 11/54 313/496
7,832,410 B2 * 11/2010 Hon ..................... A61M 11/005 128/200.14
7,896,006 B2 * 3/2011 Hamano ............. A61M 16/142 128/204.22
8,314,591 B2 * 11/2012 Terry .................... A61M 15/06 320/114
8,365,742 B2 2/2013 Hon
8,499,766 B1 * 8/2013 Newton .................. A24F 40/51 131/273
11,247,005 B2 * 2/2022 Monsalud ......... A61M 15/0035
2002/0041621 A1 * 4/2002 Faries, Jr. .............. G01K 1/143 374/147
2002/0075126 A1 * 6/2002 Reitz ...................... B82Y 30/00 338/21
2003/0033055 A1 * 2/2003 McRae ................... B05B 9/002 700/282
2003/0114795 A1 * 6/2003 Faries, Jr. ............... A61M 5/44 604/113
2004/0105163 A1 * 6/2004 Bryan .................... G02B 6/125 359/652
2004/0118401 A1 * 6/2004 Smith ............... A61M 16/0808 128/203.26
2005/0016550 A1 * 1/2005 Katase .................... A24F 40/50 131/194
2006/0047368 A1 * 3/2006 Maharajh ................ F22B 37/38 128/200.14
2006/0196518 A1 * 9/2006 Hon ......................... H02J 7/00 131/347
2007/0102013 A1 * 5/2007 Adams .................. A24F 40/485 131/273
2007/0142773 A1 * 6/2007 Rosiello .................. A61M 5/44 604/113
2007/0212510 A1 * 9/2007 Hieslmair ........... H01L 31/1804 257/E31.13
2007/0215167 A1 * 9/2007 Llewellyn Crooks ... A24C 5/00 131/335
2007/0283972 A1 * 12/2007 Monsees ................. F23Q 3/002 131/273
2008/0092912 A1 * 4/2008 Robinson ................ A24F 40/40 131/200
2008/0205481 A1 * 8/2008 Faries .................... G01K 1/146 374/138
2008/0264443 A1 * 10/2008 Shrinivasan .......... B08B 7/0021 134/2
2009/0095311 A1 * 4/2009 Han ......................... H05B 3/06 131/194
2009/0126745 A1 5/2009 Hon
2009/0188490 A1 * 7/2009 Han ...................... A61M 15/06 128/200.14
2009/0272379 A1 * 11/2009 Thorens ................... H05B 3/00 219/535
2009/0319011 A1 * 12/2009 Rosiello .................. A61M 5/44 219/494
2010/0083959 A1 * 4/2010 Siller ...................... A24F 42/60 128/202.21
2011/0011396 A1 * 1/2011 Fang .................... A61M 11/041 128/202.21
2011/0094523 A1 * 4/2011 Thorens ............... A61M 11/042 131/194
2011/0126848 A1 * 6/2011 Zuber ..................... A24F 40/46 131/329

(56) References Cited

U.S. PATENT DOCUMENTS

2011/0155718 A1* 6/2011 Greim ..................... A24F 40/70 219/539
2011/0168194 A1 7/2011 Hon
2011/0265806 A1* 11/2011 Alarcon .................. A24F 47/00 131/273
2011/0290248 A1* 12/2011 Schennum ........... B65D 83/262 128/202.21
2012/0111347 A1* 5/2012 Hon ..................... A61M 11/041 131/329
2012/0260927 A1* 10/2012 Liu ......................... A24F 40/46 219/525
2012/0279512 A1 11/2012 Hon
2012/0282132 A1* 11/2012 Watkins ................. B82Y 30/00 420/466
2012/0330234 A1* 12/2012 Balluff .................... A61M 5/44 604/114
2013/0037041 A1* 2/2013 Worm ..................... A24F 40/42 131/329
2013/0056013 A1* 3/2013 Terry ................... A61M 11/041 131/328
2013/0081625 A1* 4/2013 Rustad ................ A61M 16/109 219/553
2013/0255702 A1* 10/2013 Griffith, Jr. ............. A24F 40/70 131/328
2013/0306084 A1* 11/2013 Flick ....................... A24F 40/50 131/328
2014/0000638 A1* 1/2014 Sebastian ................ A24F 40/50 131/328
2014/0060554 A1* 3/2014 Collett .................... A24F 40/46 392/386
2014/0060555 A1* 3/2014 Chang ..................... A24F 40/40 128/202.21
2014/0096781 A1* 4/2014 Sears ...................... A24F 40/50 131/328
2014/0096782 A1* 4/2014 Ampolini ................ A24F 40/60 131/328
2014/0109921 A1* 4/2014 Chen ....................... A24F 40/44 131/273
2014/0157583 A1* 6/2014 Ward ....................... H05B 3/00 29/729
2014/0209105 A1* 7/2014 Sears ...................... A24F 40/44 131/328
2014/0253144 A1* 9/2014 Novak, III .............. A24F 40/50 324/550
2014/0261408 A1* 9/2014 DePiano ................. A24F 40/46 128/202.21
2014/0261486 A1* 9/2014 Potter ..................... A24F 40/30 131/328
2014/0261487 A1* 9/2014 Chapman ................ A24F 40/42 87/6
2014/0261495 A1* 9/2014 Novak, III ............... H05B 3/46 392/386
2014/0270727 A1* 9/2014 Ampolini ................ A24F 40/50 392/394
2014/0270729 A1* 9/2014 DePiano ................. A24F 40/46 392/397
2014/0270730 A1* 9/2014 DePiano ................. A24F 40/70 392/394
2015/0128968 A1* 5/2015 Chapman .................. A24F 7/00 131/329
2015/0128969 A1* 5/2015 Chapman ................ A24F 40/40 131/329
2015/0196060 A1* 7/2015 Wensley ............. A61M 15/002 392/404
2015/0216237 A1* 8/2015 Wensley .............. A61M 11/001 131/273
2015/0223522 A1* 8/2015 Ampolini ................ A24F 40/50 324/750.01
2015/0226432 A1* 8/2015 Borschke ................ F23Q 13/04 431/2
2015/0245669 A1* 9/2015 Cadieux .................. A24F 40/42 131/329
2015/0335070 A1* 11/2015 Sears ...................... A24F 40/40 131/328
2016/0073695 A1* 3/2016 Sears ....................... H05B 3/46 131/329
2017/0020190 A1* 1/2017 Chang .................. H05B 1/0244
2017/0020193 A1* 1/2017 Davis ................... A61M 11/042
2017/0127722 A1* 5/2017 Davis ...................... A24F 40/95
2017/0202266 A1* 7/2017 Sur ...................... A61M 11/041
2017/0215472 A1* 8/2017 Dube ..................... A24D 1/002
2018/0104425 A1* 4/2018 Hogwood ............... A24F 40/46

FOREIGN PATENT DOCUMENTS

| | | | |
|---|---|---|---|
| CN | 201379072 | | 1/2010 |
| CN | 206482012 | | 9/2017 |
| EP | 0 295 122 | | 12/1988 |
| EP | 0 845 220 | | 6/1998 |
| EP | 1 618 803 | | 1/2006 |
| GB | 2469850 | | 11/2010 |
| KR | 101412373 | | 6/2014 |
| KZ | 32979 | B | 8/2018 |
| RU | 2 602 969 | C2 | 11/2016 |
| RU | 2 611 487 | C2 | 2/2017 |
| WO | WO 2003/034847 | | 5/2003 |
| WO | WO 2004/080216 | | 9/2004 |
| WO | WO 2005/099494 | | 10/2005 |
| WO | WO 2007/131449 | | 11/2007 |
| WO | WO 2016/162446 | | 10/2016 |
| WO | WO 2017/118557 | | 7/2017 |
| WO | WO 2017/153467 | | 9/2017 |

* cited by examiner

AEROSOL DELIVERY DEVICE WITH CONDUCTIVE INSERTS

CROSS-REFERENCE TO RELATED APPLICATIONS

This application is a continuation of U.S. patent application Ser. No. 16/142,558, filed on Sep. 26, 2018, titled AEROSOL DELIVERY DEVICE WITH CONDUCTIVE INSERTS, the content of which is incorporated herein by reference in its entirety.

FIELD OF THE DISCLOSURE

The present disclosure relates to aerosol delivery articles and uses thereof for yielding tobacco components or other materials in inhalable form. More particularly, the present disclosure relates to an aerosol delivery device that utilizes electrically-generated heat to heat a tobacco or non-tobacco material, preferably without significant combustion, in order to provide an inhalable substance in the form of an aerosol for human consumption.

DESCRIPTION OF RELATED ART

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference in its entirety. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and PCT Pat. App. Pub. No. WO 2010/091593 to Hon, which are incorporated herein by reference in their entireties.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

Articles that produce the taste and sensation of smoking by electrically heating tobacco, tobacco derived materials, or other plant derived materials have suffered from inconsistent performance characteristics. For example, some articles have suffered from inconsistent release of flavors or other inhalable materials. Accordingly, it can be desirable to provide a smoking article that can provide the sensations of cigarette, cigar, or pipe smoking, that does so without combusting the substrate material, that does so without the need of a combustion heat source, and that does so with increased performance characteristics.

BRIEF SUMMARY

In various implementations, the present disclosure provides an aerosol delivery device. In one implementation, the aerosol delivery device may comprise an aerosol source member that defines an outer surface and an interior area and may include a substrate material having an aerosol precursor composition associated therewith, a control body having a housing that is configured to receive the aerosol source member, an electrical energy source coupled with the housing, and a heating assembly operatively connected to the electrical energy source. The heating assembly may include a plurality of spikes, and the plurality of spikes may be configured to articulate between a retracted position, in which the plurality of spikes are not in contact with the aerosol source member, and a heating position, in which the plurality of spikes pierces through the outer surface of the substrate material and into a portion of the interior area thereof. In some implementations, the outer surface of the substrate material may include a plurality of spaced conductive bands. In some implementations, each of the spaced conductive bands may circumscribe the entire outer surface of the substrate material. In some implementations, each of the spaced conductive bands may extend around a limited portion of the outer surface of the substrate material and may define a first end and a second end. In some implementations, in the heating position, respective spikes of the plurality of heat conducting spikes may contact the first and second ends of the spaced conductive bands. In some implementations, the plurality of spikes may comprise a heating member of the heating assembly.

In some implementations, the plurality of spaced conductive bands may comprise a heating member of the heating assembly. In some implementations, the aerosol source member further comprises a second substrate material that defines an outer surface and an interior area, and wherein the second substrate material substantially surrounds the first substrate material. In some implementations, the outer surface of the first substrate material may include a plurality of spaced conductive bands. In some implementations, each of the spaced conductive bands may circumscribe the entire outer surface of the substrate material. In some implementations, each of the spaced conductive bands may extend around a portion of the outer surface of the substrate material and may define a first end and a second end. In some implementations, in the heating position, respective spikes of the plurality of spikes may contact the first and second ends of the spaced conductive bands. In some implementations, the plurality of spikes may comprise a heating member of the heating assembly. In some implementations, the plurality of spaced conductive bands may comprise a heating member of the heating assembly. In some implementations, the substrate material may comprise at least one of a tobacco material and a tobacco-derived material. In some implementations, the substrate material may comprise a non-tobacco material. In some implementations, the first substrate material may comprise a first composition, the second substrate material may comprise a second composition, and the first composition may be different than the second composition. In some implementations, the substrate material may comprise at least one of shreds of tobacco material, beads of tobacco material, an extruded structure of tobacco material, a crimped sheet of tobacco material, and combinations thereof. In some implementations, the first substrate material may comprise at least one of shreds of tobacco material, beads of tobacco material, an extruded structure of tobacco material, a crimped sheet of tobacco material, and combinations thereof. In some implementations, the second substrate material may comprise at least one of shreds of tobacco material, beads of tobacco material, an extruded structure of tobacco material, a crimped sheet of tobacco material, and combinations thereof.

These and other features, aspects, and advantages of the disclosure will be apparent from a reading of the following detailed description together with the accompanying drawings, which are briefly described below.

BRIEF DESCRIPTION OF THE FIGURES

Figure 1:
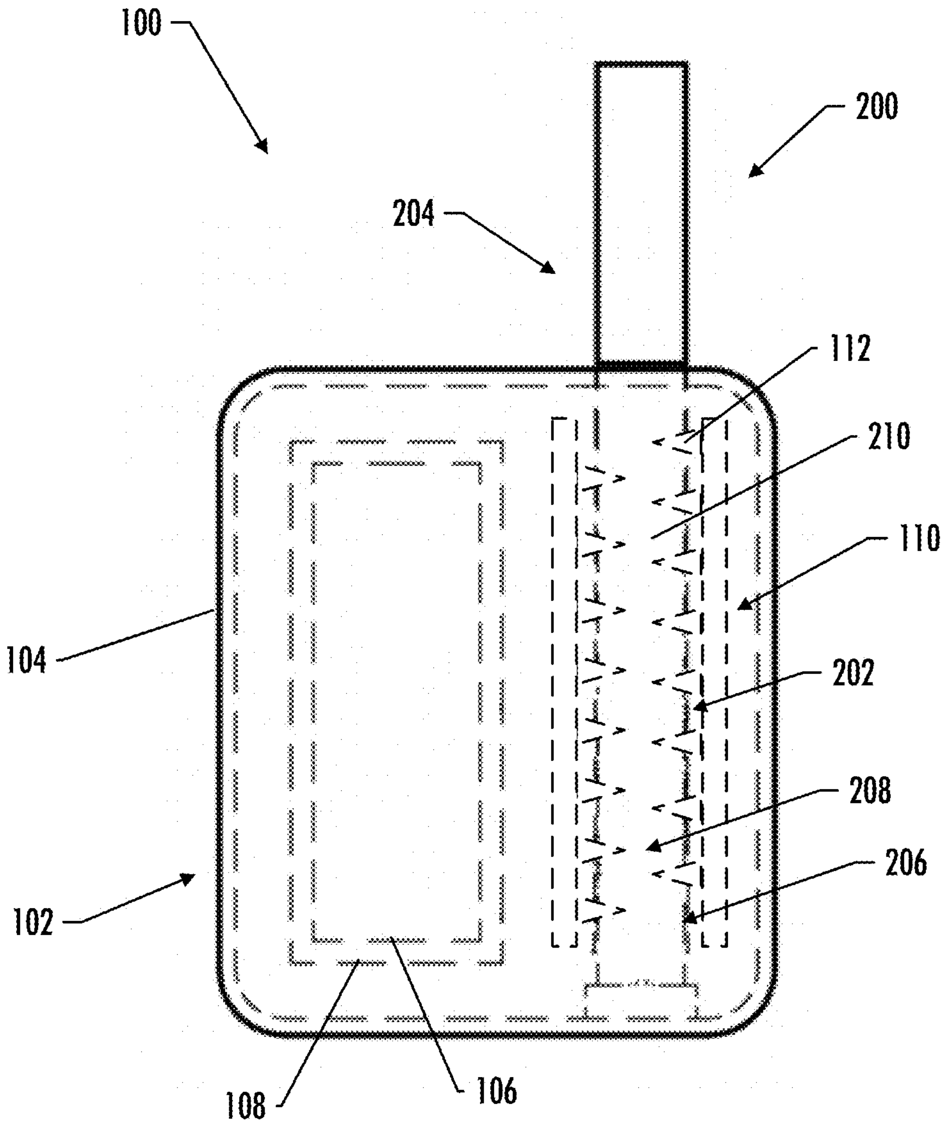
Figure 2:
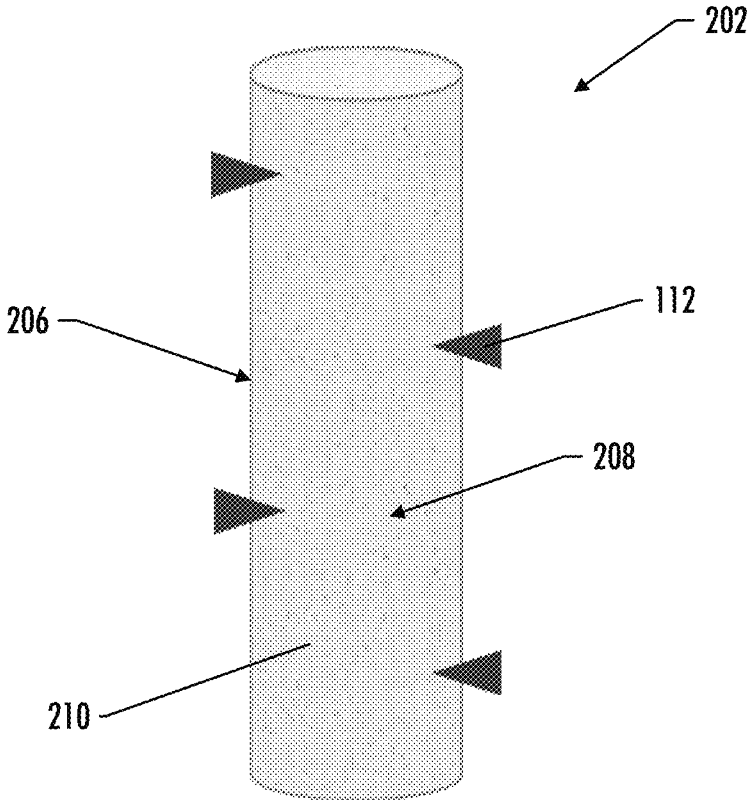
Figure 3:
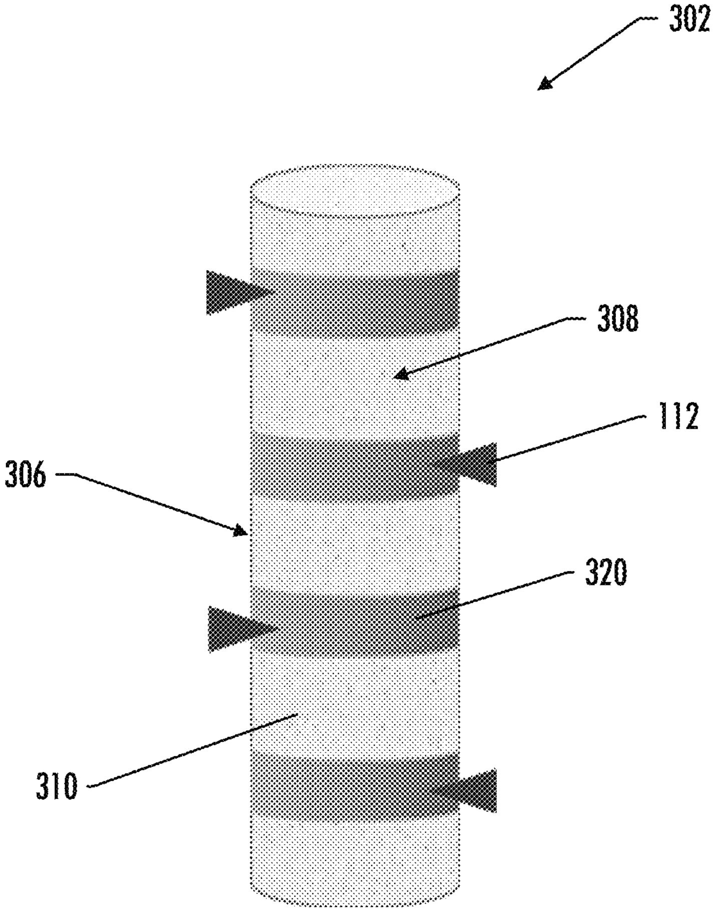
Figure 4:
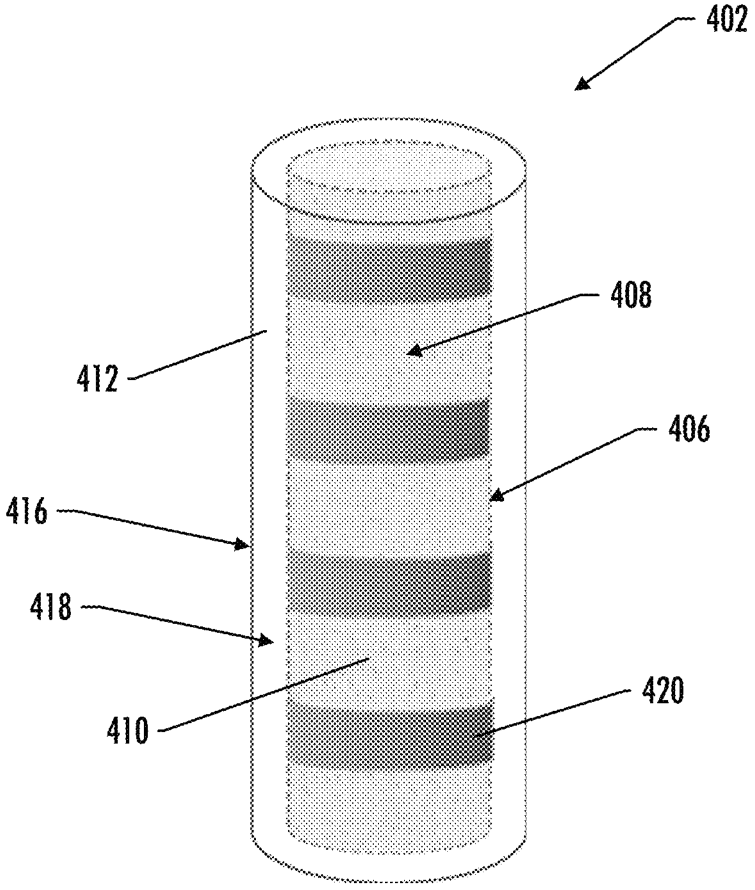
Figure 5:
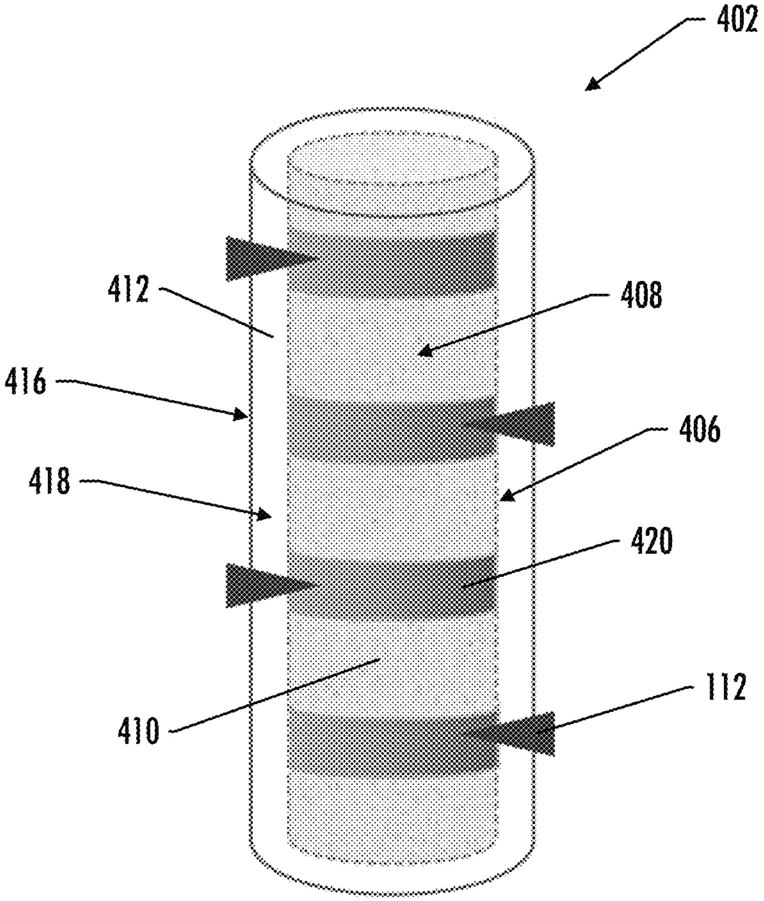
Figure 6:
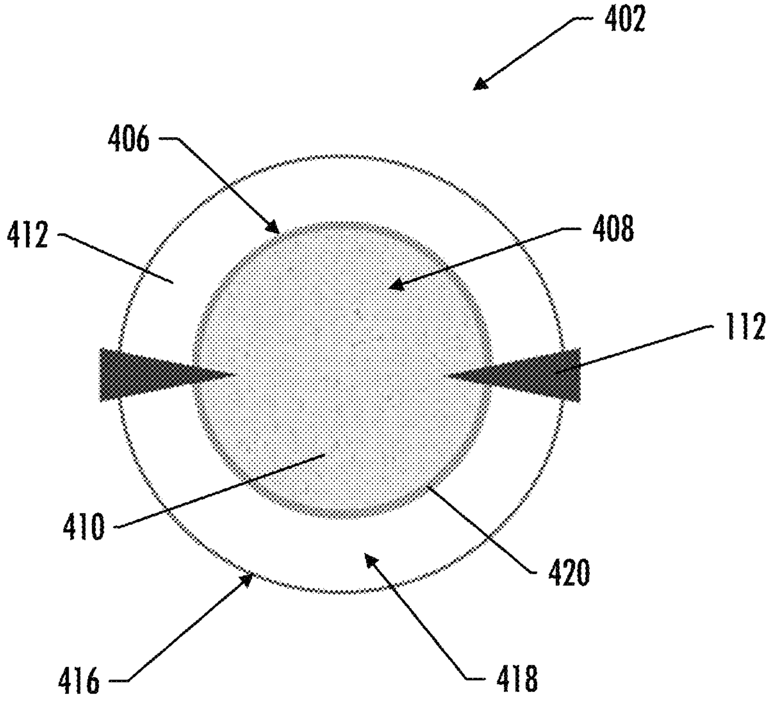
Figure 7:
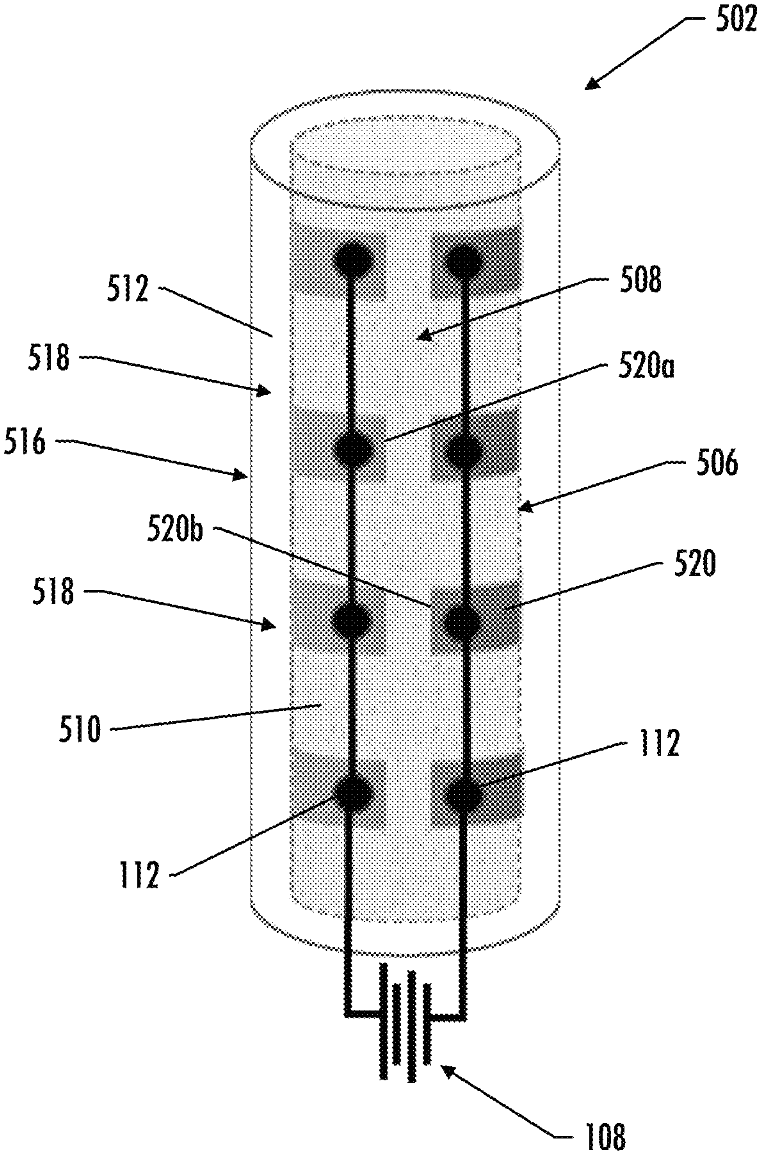
Figure 8:
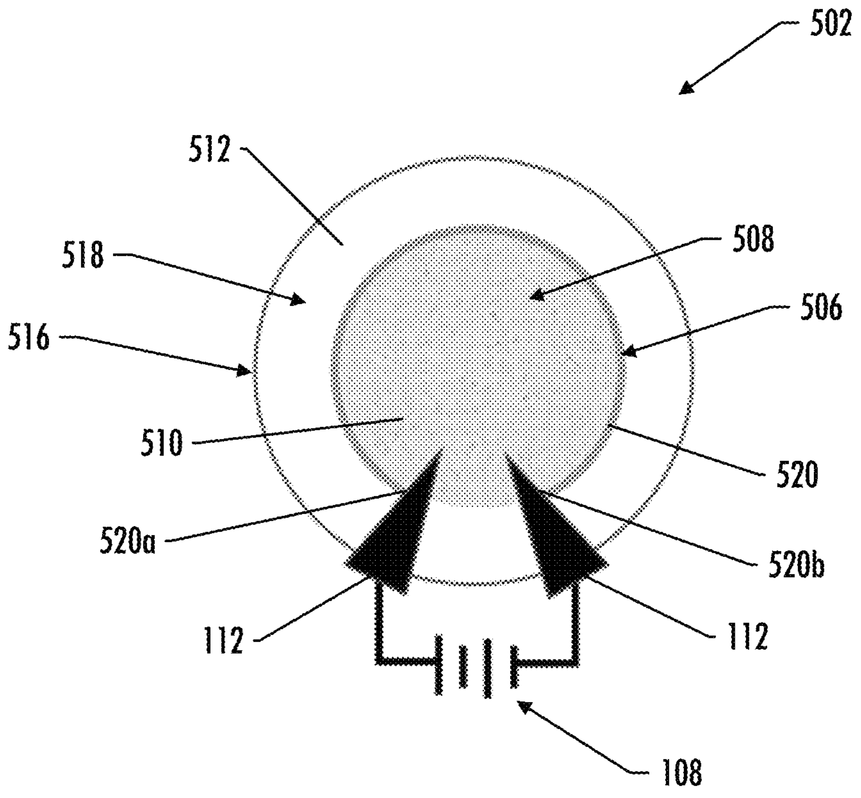

Having thus described aspects of the disclosure in the foregoing general terms, reference will now be made to the accompanying drawings, which are not necessarily drawn to scale, and wherein:

FIG. 1 illustrates a schematic front view of an aerosol delivery device comprising a control body, an aerosol source member, and a heating assembly, according to an example implementation of the present disclosure;

FIG. 2 illustrates a front schematic view of a portion of a heated end of an aerosol source member and a portion of a heating assembly, according to an example implementation of the present disclosure;

FIG. 3 illustrates a perspective schematic view of a portion of a heated end of an aerosol source member and a portion of a heating assembly, according to an example implementation of the present disclosure;

FIG. 4 illustrates a perspective schematic view of a portion of a heated end of an aerosol source member, according to an example implementation of the present disclosure;

FIG. 5 illustrates a perspective schematic view of a portion of a heated end of an aerosol source member and a portion of a heating assembly, according to an example implementation of the present disclosure;

FIG. 6 illustrates a top schematic view of a heated end of an aerosol source member and a portion of a heating assembly, according to an example implementation of the present disclosure;

FIG. 7 illustrates a perspective schematic drawing of a portion of a heated end an aerosol source member and a portion of a heating assembly, according to an example implementation of the present disclosure; and FIG. 8 illustrates a top schematic view of a heated end of an aerosol source member and a portion of a heating assembly, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices for use with aerosol source members. Aerosol delivery devices according to the present disclosure use electrical energy to heat a material (preferably without combusting the material to any significant degree) to form an inhalable substance; and components of such systems have the form of articles that are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called “e-cigarettes” or “tobacco heating products,” it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term “aerosol” as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some implementations, the terms may be interchangeable. Thus, for simplicity, the terms as used to describe aspects of the disclosure are understood to be interchangeable unless stated otherwise.

Aerosol delivery devices of the present disclosure generally include a number of components provided within an outer body or shell, which may be referred to as a housing. The overall design of the outer body or shell may vary, and the format or configuration of the outer body that may define the overall size and shape of the aerosol delivery device may vary. Typically, an elongate body resembling the shape of a cigarette or cigar, or a fob-shaped body, may be a formed from a single, unitary housing or the housing can be formed of two or more separable bodies. For example, an aerosol delivery device may comprise an elongated shell or body that may be substantially tubular in shape and, as such, resemble the shape of a conventional cigarette or cigar. In another example, an aerosol delivery device may have a box or fob shape. In one example, all of the components of the aerosol delivery device are contained within one housing. Alternatively, an aerosol delivery device may comprise two or more housings that are joined and are separable. For example, an aerosol delivery device may possess a control body comprising a housing containing one or more reusable components (e.g., an accumulator such as a rechargeable battery and/or rechargeable supercapacitor, and various electronics for controlling the operation of that article), removably coupleable thereto, a disposable portion (e.g., a disposable flavor-containing aerosol source member). More specific formats, configurations and arrangements of components within the single housing type of unit or within a multi-piece separable housing type of unit will be evident in light of the further disclosure provided herein. Additionally, various aerosol delivery device designs and component arrangements may be appreciated upon consideration of the commercially available electronic aerosol delivery devices.

As will be discussed in more detail below, aerosol delivery devices of the present disclosure may comprise some combination of a power source (i.e., an electrical energy source), at least one control component (e.g., means for actuating, controlling, regulating and ceasing power for heat generation, such as by controlling electrical current flow from the electrical energy source to other components of the device—e.g., a microprocessor, individually or as part of a microcontroller), a heater or heat generation member (e.g., an electrical resistance heating element or other component and/or an inductive coil or other associated components and/or one or more radiant heating elements), and an aerosol source member that includes a substrate material capable of yielding an aerosol upon application of sufficient heat. In various implementations, the aerosol source member may include a mouth end or tip configured to allow drawing upon the aerosol delivery device for aerosol inhalation (e.g., a defined airflow path through the device such that aerosol generated can be withdrawn therefrom upon draw).

Alignment of the components within the aerosol delivery device of the present disclosure may vary across various implementations. In some implementations, substrate material of an aerosol source member may be positioned proximate a heating member so as to maximize aerosol delivery to the user. Other configurations, however, are not excluded. Generally, the heating member may be positioned sufficiently near the substrate material so that heat from the heating member can volatilize the substrate material (as well as, in some implementations, one or more flavourants, medicaments, or the like that may likewise be provided for delivery to a user) and form an aerosol for delivery to the user. When the heating member heats the substrate material, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device of various implementations may incorporate a battery and/or other electrical source to provide current flow sufficient to provide various functionalities to the aerosol delivery device, such as powering of a heating member, powering of control systems, powering of indicators, and the like. As will be discussed in more detail below, the electrical energy source may take on various implementations. Preferably, the electrical energy source may be able to deliver sufficient power to rapidly activate the heating member to provide for aerosol formation and power the aerosol delivery device through use for a desired duration of time. The electrical energy source is preferably sized to fit conveniently within the aerosol delivery device so that the aerosol delivery device can be easily handled.

In further implementations, the electrical energy source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the device. Thus, the device may also include a charger component that can be attached to the smoking device between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the device (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In another example, a personal vaporizer unit may comprise a first conductive surface configured to contact a first body part of a user holding the personal vaporizer unit, and a second conductive surface, conductively isolated from the first conductive surface, configured to contact a second body part of the user. As such, when the personal vaporizer unit detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S.

Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

More specific formats, configurations and arrangements of various substrate materials, aerosol source members, and components within aerosol delivery devices of the present disclosure will be evident in light of the further disclosure provided hereinafter. Additionally, the selection of various aerosol delivery device components may be appreciated upon consideration of the commercially available electronic aerosol delivery devices. Further, the arrangement of the components within the aerosol delivery device may also be appreciated upon consideration of the commercially available electronic aerosol delivery devices.

A front schematic illustration of an example implementation of an aerosol delivery device 100 in accordance with the present disclosure is shown in FIG. 1. In general, the aerosol delivery device 100 of the depicted implementation includes a control body 102 that includes a housing 104 configured to receive an aerosol source member 200. In the depicted implementation, the control body 102 may also include a control component 106 (e.g., a microprocessor, individually or as part of a microcontroller, a printed circuit board (PCB) that includes a microprocessor and/or microcontroller, etc.) and an electrical energy source 108 (e.g., a battery, which may be rechargeable, and/or a rechargeable supercapacitor). In various implementations, one or both of the control component 106 and the electrical energy source 108 may be coupled with the housing 104. For the sake of the current application, the phrase "coupled with" when used with respect to one component relative to another may encompass implementations in which one component is located within another component and/or implementations wherein one component is separate but otherwise operatively connected to another component. For example, in the depicted implementation, both the control component 106 and the electrical energy source 108 are located within the housing; however, in other implementations one or both of the control component 106 and the electrical energy source 108 may be separate components. Further information regarding the control component 106 and the electrical energy source 108 is provided below. In some implementations, the housing 104 may also include a pushbutton configured to activate certain operations of the device 100, such as, for example, turning on the device and initiating heating of a heating member. In various implementations, the aerosol source member 200 may comprise a heated end 202, which is configured to be inserted into the control body 102, and a mouth end 204, upon which a user draws to create the aerosol. It should be noted that while the aerosol delivery device of FIG. 1 is shown as having a substantially rectangular or fob-shaped control body 102 for ease of illustration, in other implementations the control body 102 may have any other shape including an elongated shell or body that may be substantially tubular in shape and, as such, resemble the shape of a conventional cigarette or cigar, and thus the components described below may be sized and configured to fit inside an elongated body.

In specific implementations, one or both of the control body 102 and the aerosol source member 200 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 200 may comprise a single-use device. A single use component for use with a control body is disclosed in U.S. Pat. No. 8,910,639 to Chang et al., which is incorporated herein by reference in its entirety.

As noted above, the control body 102 may further include a control component 106. For example, the control component 106 may comprise a control circuit (which may be connected to further components, as further described herein) that may be connected by electrically conductive wires to the electrical energy source 108. In various implementations, the control component 106 may control when and how the heating member receives electrical energy to heat the inhalable substance medium for release of the inhalable substance for inhalation by a consumer. Such control can relate to actuation of pressure sensitive switches or the like, which are described in greater detail hereinafter. It should be noted that the terms "connected" or "coupled" should not be read as necessitating direct connection without an intervening component. Rather, these terms may encompass direct connection and/or connection via one or more intervening components. As such, in various implementations these terms may be understood to mean operatively connected to or operatively coupled with.

In various implementations, the control component 106 may also be configured to closely control the amount of heat provided to the substrate material. While the heat needed to volatilize the aerosol-forming substance in a sufficient volume to provide a desired dosing of the inhalable substance for a single puff can vary for each particular substance used, it can be particularly useful for the heating member to heat to a temperature of at least 120° C., at least 130° C., or at least 140° C. In some implementations, in order to volatilize an appropriate amount of the aerosol-forming substance and thus provide a desired dosing of the inhalable substance, the heating temperature may be at least 150° C., at least 200° C., at least 300° C., or at least 350° C. It can be particularly desirable, however, to avoid heating to temperatures substantially in excess of about 550° C. in order to avoid degradation and/or excessive, premature volatilization of the aerosol-forming substance. Heating specifically should be at a sufficiently low temperature and sufficiently short time so as to avoid significant combustion (preferably any combustion) of the inhalable substance medium. The present disclosure may particularly provide the components of the present article in combinations and modes of use that will yield the inhalable substance in desired amounts at relatively low temperatures. As such, yielding can refer to one or both of generation of the aerosol within the article and delivery out of the article to a consumer. In specific implementations, the heating temperature may be about 120° C. to about 300° C., about 130° C. to about 290° C., about 140° C. to about 280° C., about 150° C. to about 250° C., or about 160° C. to about 200° C. The duration of heating can be controlled by a number of factors, as discussed in greater detail hereinbelow. Heating temperature and duration may depend upon the desired volume of aerosol and ambient air that is desired to be drawn through the aerosol source member, as further described herein. The duration, however, may be varied depending upon the heating rate of the heating member, as the article may be configured such that the heating member is energized only until a desired temperature is reached. Alternatively, duration of heating may be coupled to the duration of a puff on the article by a consumer. Generally, the temperature and time of heating will be controlled by one or more components contained in the control body, as noted above.

The amount of inhalable material released by the aerosol source member can vary based upon the nature of the inhalable material. Preferably, the aerosol source member is configured with a sufficient amount of the inhalable material, with a sufficient amount of any aerosol-former, and to function at a sufficient temperature for a sufficient time to release a desired amount over a course of use. The amount may be provided in a single inhalation from the aerosol source member or may be divided so as to be provided through a number of puffs from the article over a relatively short length of time (e.g., less than 30 minutes, less than 20 minutes, less than 15 minutes, less than 10 minutes, or less than 5 minutes). For example, the device may provide nicotine in an amount of about 0.05 mg to about 1.0 mg, about 0.08 mg to about 0.5 mg, about 0.1 mg to about 0.3 mg, or about 0.15 mg to about 0.25 mg per puff on the aerosol source member. In other implementations, a desired amount may be characterized in relation to the amount of wet total particulate matter delivered based on puff duration and volume. For example, the aerosol source member may deliver at least 1.0 mg of wet total particulate matter on each puff, for a defined number of puffs (as otherwise described herein), when smoked under standard FTC smoking conditions of 2 second, 35 ml puffs. Such testing may be carried out using any standard smoking machine. In other implementations, the amount of total particulate matter (TPM) yielded under the same conditions on each puff may be at least 1.5 mg, at least 1.7 mg, at least 2.0 mg, at least 2.5 mg, at least 3.0 mg, about 1.0 mg to about 5.0 mg, about 1.5 mg to about 4.0 mg, about 2.0 mg to about 4.0 mg, or about 2.0 mg to about 3.0 mg.

As noted, the aerosol delivery device 100 of some implementations may include a pushbutton, which may be linked to the control component for manual control of the heating assembly 110. For example, in some implementations the consumer may use the pushbutton to energize the heating assembly 110. Similar functionality tied to the pushbutton may be achieved by other mechanical means or non-mechanical means (e.g., magnetic or electromagnetic). Thusly, activation of the heating assembly 110 may be controlled by a single pushbutton. Alternatively, multiple pushbuttons may be provided to control various actions separately. One or more pushbuttons present may be substantially flush with the casing of the control body 102.

Instead of (or in addition to) any pushbuttons, the aerosol delivery device 100 of the present disclosure may include components that energize the heating assembly 110 in response to the consumer's drawing on the article (i.e., puff-actuated heating). For example, the device may include a switch or flow sensor (not shown) in the control body 102 that is sensitive either to pressure changes or air flow changes as the consumer draws on the article (i.e., a puff-actuated switch). Other suitable current actuation/deactuation mechanisms may include a temperature actuated on/off switch or a lip pressure actuated switch. An exemplary mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the consumer draws on the device. In addition, flow sensing devices, such as those using hot-wire anemometry principles, may be used to cause the energizing of the heating assembly sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and aerosol source member 200 may be included in the control body 102 so that pressure changes during draw are readily identified by the switch. Other exemplary puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

When the consumer draws on the mouth end of the device 100, the current actuation means may permit unrestricted or uninterrupted flow of current through the heating assembly generate heat rapidly. Because of the rapid heating, it can be useful to include current regulating components to (i) regulate current flow through the heating member to control heating of the resistance element and the temperature experienced thereby, and (ii) prevent overheating and degradation of the substrate material 210. In some implementations, the current regulating circuit may be time-based. Specifically, such a circuit may include a means for permitting uninterrupted current flow through the heating member for an initial time period during draw, and a timer means for subsequently regulating current flow until draw is completed. For example, the subsequent regulation can include the rapid on-off switching of current flow (e.g., on the order of about every 1 to 50 milliseconds) to maintain the heating member within the desired temperature range. Further, regulation may comprise simply allowing uninterrupted current flow until the desired temperature is achieved then turning off the current flow completely. The heating member may be reactivated by the consumer initiating another puff on the article (or manually actuating the pushbutton, depending upon the specific switch implementation employed for activating the heater). Alternatively, the subsequent regulation can involve the modulation of current flow through the heating member to maintain the heating member within a desired temperature range. In some implementations, so as to release the desired dosing of the inhalable substance, the heating member may be energized for a duration of about 0.2 second to about 5.0 seconds, about 0.3 second to about 4.0 seconds, about 0.4 second to about 3.0 seconds, about 0.5 second to about 2.0 seconds, or about 0.6 second to about 1.5 seconds. One exemplary time-based current regulating circuit can include a transistor, a timer, a comparator, and a capacitor. Suitable transistors, timers, comparators, and capacitors are commercially available and will be apparent to the skilled artisan. Exemplary timers are those available from NEC Electronics as C-1555C and from General Electric Intersil, Inc. as ICM7555, as well as various other sizes and configurations of so-called "555 Timers". An exemplary comparator is available from National Semiconductor as LM311. Further description of such time-based current regulating circuits is provided in U.S. Pat. No. 4,947,874 to Brooks et al., which is incorporated herein by reference in its entirety.

In light of the foregoing, it can be seen that a variety of mechanisms can be employed to facilitate actuation/deactuation of current to the heating member. For example, the device may include a timer for regulating current flow in the article (such as during draw by a consumer). The device may further include a timer responsive switch that enables and disables current flow to the heating member. Current flow regulation also can comprise use of a capacitor and components for charging and discharging the capacitor at a defined rate (e.g., a rate that approximates a rate at which the heating member heats and cools). Current flow specifically may be regulated such that there is uninterrupted current flow through the heating member for an initial time period during draw, but the current flow may be turned off or cycled alternately off and on after the initial time period until draw is completed. Such cycling may be controlled by a timer, as discussed above, which can generate a preset switching cycle. In specific implementations, the timer may generate a periodic digital wave form. The flow during the initial time period further may be regulated by use of a comparator that compares a first voltage at a first input to a threshold voltage at a threshold input and generates an output signal when the first voltage is equal to the threshold voltage, which enables the timer. Such implementations further can include components for generating the threshold voltage at the threshold input and components for generating the threshold voltage at the first input upon passage of the initial time period.

As noted above, the electrical energy source 108 used to provide power to the various electrical components of the device 100 may take on various implementations. Preferably, the electrical energy source is able to deliver sufficient energy to rapidly heat the heating assembly in the manner described above and power the device through use with multiple aerosol source members 200 while still fitting conveniently in the device 100. Examples of useful electrical energy sources include lithium-ion batteries that are preferably rechargeable (e.g., a rechargeable lithium-manganese dioxide battery). In particular, lithium polymer batteries can be used as such batteries can provide increased safety. Other types of batteries—e.g., nickel-cadmium cells—may also be used. Additionally, a preferred electrical energy source is of a sufficiently light weight to not detract from a desirable smoking experience. Some examples of possible electrical energy sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

One example of an electrical energy source is a TKI-1550 rechargeable lithium-ion battery produced by Tadiran Batteries GmbH of Germany. In another implementation, a useful electrical energy source may be a N50-AAA CADNICA nickel-cadmium cell produced by Sanyo Electric Company, Ltd., of Japan. In other implementations, a plurality of such batteries, for example providing 1.2-volts each, may be connected in series. Other electrical energy sources, such as rechargeable lithium-manganese dioxide batteries, may also be used. Any of these batteries or combinations thereof may be used in the electrical energy source, but rechargeable batteries are preferred because of cost and disposal considerations associated with disposable batteries. In implementations where rechargeable batteries are used, the aerosol delivery device 100 may further include charging contacts for interaction with corresponding contacts in a conventional recharging unit (not shown) deriving power from a standard 120-volt AC wall outlet, or other sources such as an automobile electrical system or a separate portable power supply. In further implementations, the electrical energy source may also comprise a capacitor. Capacitors are capable of discharging more quickly than batteries and can be charged between puffs, allowing the battery to discharge into the capacitor at a lower rate than if it were used to power the heating member directly. For example, a supercapacitor—i.e., an electric double-layer capacitor (EDLC)—may be used separate from or in combination with a battery. When used alone, the supercapacitor may be recharged before each use of the device 100. Thus, the present disclosure also may include a charger component that can be attached to the device between uses to replenish the supercapacitor. Thin film batteries may be used in certain implementations of the present disclosure.

As noted above, in various implementations, the aerosol delivery device 100 may comprise one or more indicators (not shown). In various implementations, one or more indicators may be located at any location on the control body 102. In some implementations, the indicators may be lights (e.g., light emitting diodes) that may provide indication of multiple aspects of use of the device. For example, a series of lights may correspond to the number of puffs for a given aerosol source member. Specifically, the lights may successively become lit with each puff such that when all lights are lit, the consumer is informed that the aerosol source member is spent. Alternatively, all lights may be lit upon the aerosol source member being inserted into the housing, and a light may turn off with each puff, such that when all lights are off, the consumer is informed that the aerosol source member is spent. In still other implementations, only a single indicator may be present, and lighting thereof may indicate that current was flowing to the heating member and the device is actively heating. This may ensure that a consumer does not unknowingly leave the device unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the present disclosure. Moreover, combinations of such indicators also may be used in a single device.

In various implementations, the housing 104 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as further discussed herein. In some implementations, a heat resistant polymer may be used. In other implementations, ceramic materials may be used. In further implementations, an insulating material may be used so as not to unnecessarily move heat away from the aerosol source member. The housing, when formed of a single layer, may have a thickness that preferably is about 0.2 mm to about 5.0 mm, about 0.5 mm to about 4.0 mm, about 0.5 mm to about 3.0 mm, or about 1.0 mm to about 3.0 mm. Further example types of components and materials that may be used to provide the functions described above or be used as alternatives to the materials and components noted above can be those of the types set forth in U.S. Pat. App. Pub. Nos. 2010/00186757 to Crooks et al.; 2010/00186757 to Crooks et al.; and 2011/0041861 to Sebastian et al.; the disclosures of the documents being incorporated herein by reference in their entireties.

Referring to FIGS. 1 and 2, the aerosol source member 200 defines an outer surface 206 and an interior area 208. In the depicted implementation, a substrate material 210 is located in the interior area 208 of the heated end 202 of the aerosol source member 200. In some implementations, however, substrate material may be located in both the heated end 202 and the mouth end 204 of the aerosol source member 200. In the depicted implementation, the substrate material 210 has a single segment, although in other implementations the substrate material 210 may include additional segments, which may have different compositions. For example, the heated end 202 of some implementations of the aerosol source member 200 may further comprise a second substrate material segment (not shown). In various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions, components, and/or additives for use in a substrate material (and/or substrate materials) are described in more detail below. It should be noted that the subsequent discussion should be applicable to any substrate material or substrate material segment usable in the aerosol delivery devices described herein.

In various implementations, the aerosol source member 200, or a portion thereof, may be wrapped in an exterior overwrap material. In various implementations, the mouth end 204 of the aerosol source member 200 may include a filter, which may, for example, be made of a cellulose acetate or polypropylene material. The filter may additionally or alternatively contain strands of tobacco containing material, such as described in U.S. Pat. No. 5,025,814 to Raker et al., which is incorporated herein by reference in its entirety. In various implementations, the filter may increase the structural integrity of the mouth end of the aerosol source member, and/or provide filtering capacity, if desired, and/or provide resistance to draw. The exterior overwrap material may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the exterior overwrap at the mouth end 204 of the aerosol source member may function to simply separate the substrate material from the mouth of a consumer or to provide space for positioning of a filter material, as described below, or to affect draw on the article or to affect flow characteristics of the vapor or aerosol leaving the device during draw. Further discussions relating to the configurations for exterior overwrap materials that may be used with the present disclosure may be found in U.S. Pat. No. 9,078,473 to Worm et al., which is incorporated herein by reference in its entirety.

In general, the shape and dimensions of the aerosol source member of the various implementations described herein will depend on the size of the housing, the physics of heat and mass transfer for the geometric design, and/or the expected number of puffs of the aerosol source member. Although a variety of different shapes (e.g., cylindrical, cuboidal, spherical, etc.) and dimensions are possible, in some implementations, an aerosol source member having a cylindrical shape may have an overall diameter of approximately 5.4 mm and a length of approximately 83 mm. In other implementations, the aerosol source member may have an overall diameter of approximately 7-8 mm (such as, for example, approximately 7.8 mm) or larger. In other implementations, an aerosol source member having a cuboidal shape may have dimensions of approximately 70 mm×20 mm×6 mm. In any of these examples, the dimensions may vary greatly, such as, for example, ±50% variation in any dimension.

In various implementations, heating of the substrate material 210 results in aerosolization of the aerosol precursor composition associated with the substrate material 210. In various implementations, the mouth end 204 of the aerosol source member 200 is configured to receive the generated aerosol therethrough in response to a draw applied to the mouth end 204 by a user. As noted, the mouth end 204 of the aerosol source member 200 of some implementations may include a filter configured to receive the aerosol therethrough in response to the draw applied to the mouth end 204 of the aerosol source member. Preferably, the elements of the substrate material 210 do not experience thermal decomposition (e.g., charring, scorching, or burning) to any significant degree, and the aerosolized components are entrained in the air that is drawn through the aerosol delivery device 100, including a filter (if present), and into the mouth of the user.

In one implementation, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise a crimped sheet of reconstituted tobacco material. In some implementations, the substrate material may comprise overlapping layers (e.g., a gathered web), which may, or may not, include heat conducting constituents. Examples of substrate materials that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, one or more of the substrate materials may include a plurality of microcapsules each formed into a hollow cylindrical shape. In some implementations, one or more of the substrate materials may include a binder material configured to maintain the structural shape and/or integrity of the plurality of microcapsules formed into the hollow cylindrical shape.

Tobacco employed in one or more of the substrate materials may include, or may be derived from, tobaccos such as flue-cured tobacco, burley tobacco, Oriental tobacco, Maryland tobacco, dark tobacco, dark-fired tobacco and Rustica tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.,* 39, p. 11-17 (1997); the disclosures of which are incorporated herein by reference in their entireties.

In still other implementations of the present disclosure, the substrate material may include an extruded structure that includes, or is essentially comprised of a tobacco, a tobacco related material, glycerin, water, and/or a binder material, although certain formulations may exclude the binder material. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise microcellulose or nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

Additionally or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate may remain substantially solid throughout the aerosol-generating process and may substantially maintain structural integrity throughout the aerosol-generating process. Example tobacco and/or tobacco related materials suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In some implementations, the amount of substrate material that is used within the aerosol delivery device may be such that the article exhibits acceptable sensory and organoleptic properties, and desirable performance characteristics. For example, in some implementations the aerosol precursor composition such as, for example, glycerin and/or propylene glycol, may be employed within the substrate material in order to provide for the generation of a visible mainstream aerosol that in many regards resembles the appearance of tobacco smoke.

Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some aspects, a substrate material may produce a visible aerosol upon the application of sufficient heat thereto (and cooling with air, if necessary), and the substrate material may produce an aerosol that is "smoke-like." In other aspects, the substrate material may produce an aerosol that is substantially non-visible but is recognized as present by other characteristics, such as flavor or texture. Thus, the nature of the produced aerosol may be variable depending upon the specific components of the aerosol delivery component. The substrate material may be chemically simple relative to the chemical nature of the smoke produced by burning tobacco.

According to another implementation, an aerosol delivery device according to the present disclosure may include a substrate material comprising a porous, inert material such as, for example, a ceramic material. For example, in some implementations ceramics of various shapes and geometries (e.g., beads, rods, tubes, etc.) may be used, which have various pore morphology. In addition, in some implementations non-tobacco materials, such as e-liquids, may be loaded into the ceramics. In another implementation, the substrate material may include a porous, inert material that does not substantially react, chemically and/or physically, with a tobacco-related material such as, for example, a tobacco-derived extract. In addition, an extruded tobacco, such as those described above, may be porous. For example, in some implementations an extruded tobacco material may have an inert gas, such as, for example, nitrogen, that acts as a blowing agent during the extrusion process.

As noted above, in various implementations one or more of the substrate materials may include a tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a flame/burn retardant (e.g., diammonium phosphate and/or another salt) configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

As noted, in some implementations flame/burn retardant materials and other additives that may be included within one or more of the substrate materials and may include organo-phosphorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, and pyruvic acid, may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In other implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organophosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired property of flame-retardancy without undesirable off-gassing or melting-type behavior.

In the depicted implementation, a cross-section of the aerosol source member 200 may be substantially circular such that the aerosol source member 200 defines a substantially cylindrical shape extending between the opposed first and second ends thereof. However, in other implementations, the aerosol source member 200 may define a substantially non-circular cross-section such that the aerosol source member 200 may define a substantially non-cylindrical shape between the opposed first and second ends thereof. Otherwise, in other examples, the aerosol source member 200 may comprise an asymmetric cross-section about the axis.

Although not depicted in the figures, the housing 104 may include one or more apertures therein for allowing entrance of ambient air to be directed into the heated end 202 of the aerosol source member 200. Thus, when a consumer draws on the mouth end 204 of the aerosol source member 200, air can pass into the aerosol source member 200 proximate the heated end 202, and be drawn through the inhalable substance medium for inhalation by the consumer through the mouth end 204. As will be discussed in more detail below, in implementations wherein the overwrap is present, the drawn air may carry the inhalable substance through the optional filter and out of an opening of the overwrap.

In some implementations, the control body 102 may include a flow sensor (not shown, e.g., a puff sensor or pressure switch). In other implementations, the control body 102 may alternately, or in addition, include an activation button (not shown). With respect to a flow sensor, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery devices and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. patent application Ser. No. 14/881,392 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

In some implementations, an input element may be included with the aerosol delivery device (and may replace or supplement an airflow or pressure sensor). The input element may be included to allow a user to control functions of the device and/or for output of information to a user. Any component or combination of components may be utilized as an input element for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference. As still a further example, a capacitive sensor may be implemented on the aerosol delivery device to enable a user to provide input, such as by touching a surface of the device on which the capacitive sensor is implemented.

As noted, the aerosol delivery device 100 of the depicted implementation also includes a heating assembly 110, which receives power from the electrical energy source 108 and, in some implementations, may be controlled by the control component 106. In various implementations, the heating assembly 110 may include a heating member that may be any device suitable to provide heat sufficient to facilitate release of the inhalable substance for inhalation by a consumer. In certain implementations, the electrical heating member may be a resistance heating member. Useful heating members can be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time based current control is employed. Useful heating members also are chemically non-reactive (and chemically non-catalytic) with the materials comprising the inhalable substance medium being heated so as not to adversely affect the flavor or content of the aerosol or vapor that is produced. Example, non-limiting, materials that may comprise the heating member include a variety of metal and ceramic materials. Other specific non-limiting examples include carbon, graphite, carbon/graphite composites, metallic and non-metallic carbides, nitrides, silicides, inter-metallic compounds, cermets, metal alloys, and metal foils. In particular, refractory materials may be useful. Various, different materials can be mixed to achieve the desired properties of resistivity, mass, thermal conductivity, and surface properties.

In some implementations, the heating member may be provided in other forms, such as in the form of a foil, a foam, a mesh, a hollow ball, a half ball, discs, spirals, fibers, wires, films, yarns, strips, ribbons, or cylinders. Such heating members often comprise a metal material and are configured to produce heat as a result of the electrical resistance associated with passing an electrical current therethrough. Such resistive heating elements may be positioned in proximity to, and/or in direct contact with, the substrate portion. The heating assembly or the heating member may be located in the control body and/or the aerosol source member, as will be discussed in more detail below. In various implementations, the substrate portion may include components (i.e., heat conducting constituents) that are imbedded in, or otherwise part of, the substrate portion that may serve as, or facilitate the function of, the heating assembly. Some examples of various heating members and elements are described in U.S. Pat. No. 9,078,473 to Worm et al., the disclosure of which is incorporated herein by reference in its entirety.

Some non-limiting examples of various heating member configurations include configurations in which a heating member or element is placed in proximity with an aerosol source member. For instance, in some examples, at least a portion of a heating member may surround at least a portion of an aerosol source member. In other examples, one or more heating members may be positioned adjacent an exterior of an aerosol source member when inserted in a control body. In other examples, at least a portion of a heating member may penetrate at least a portion of an aerosol source member (such as, for example, one or more prongs and/or spikes that penetrate an aerosol source member), when the aerosol source member is inserted into the control body.

Various embodiments of materials configured to produce heat when electrical current is applied therethrough may be employed to form the heating member. Example materials from which the wire coil may be formed include Kanthal (FeCrAl), nichrome, nickel, stainless steel, indium tin oxide, tungsten, molybdenum disilicide ($MoSi_2$), molybdenum silicide (MoSi), molybdenum disilicide doped with aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). The heating member may be resistive heating member or a heating member configured to generate heat through induction. The heating member may be coated by heat conductive ceramics such as aluminum nitride, silicon carbide, beryllium oxide, alumina, silicon nitride, or their composites.

As will be discussed in more detail below, in some of the depicted implementations a plurality of spikes serve as the heating member. In other of the depicted implementations, a plurality of spaced bands serve as the heating member in addition to the plurality of spikes or as an alternate to the plurality of spikes.

As shown in FIG. 1, the heating assembly 110 includes a plurality of spikes 112 that are configured to articulate between a retracted position, in which the spikes are not in contact with aerosol source member, and a heating position, in which spikes contact the aerosol source member 200. In particular, FIG. 1 shows the spikes 112 in a heating position. In various implementations of the heating position, the spikes not only contact the aerosol source member 200 but also pierce through the outer surface 206 of the aerosol source member 200 such that a portion of the spikes 112 extends into the substrate material 210. In various implementations, the degree to which the spikes 112 extend into the substrate material may vary. For example, in some implementations the spikes 112 may extend into the substrate material a small distance, while in other implementations the spikes 112 may extend to the center of the substrate material 210, and in still other implementations, the spikes 112 may extend through the center of the substrate material 210.

In various implementations, the plurality of spikes 112 may comprise opposing rows of spikes 112, such as those illustrated in FIGS. 1 and 2, with one row being positioned on one side of the aerosol source member 200, and the other row being positioned on an opposite side of the aerosol source member 200. It should be noted that in some implementations, there may be additional rows of spikes 112, such as, for example, three or more rows that may be positioned around a circumference of the heated end 202 of the aerosol source member 200. In other implementations, however, there may be a single row of spikes 112. In some implementations, the positioning of the individual spikes 112 may be staggered between the rows, such as those illustrated in FIGS. 1 and 2, while in other implementations the positioning of the individual spikes 112 may be substantially aligned. In various implementations, articulation of the plurality of spikes 112 may occur in different ways. For example, in some implementations the plurality of spikes 112 may be contained in a clamshell housing that moves away from the aerosol source member 200 in the retracted position and toward the aerosol source member 200 in the heating position. In some implementations, activation of the articulating motion may be triggered by a button. For example, in some implementations the clamshell housing may be spring-loaded, and a button may trigger the clamshell housing to move from the retracted position to the heating position. In another implementation, a user may slide a feature that carries one or both of the rows of spikes 112 from the retracted position to the heating position, in which the spikes 112 pierce through the outer surface 206 of the substrate material and into a portion of the interior area 208 thereof. It should be noted that although in the implementations shown in the figures, the spikes have been schematically illustrated as having a substantially cone-like shape, in various other implementations the spikes may have a variety of other shapes configured to allow the spikes to pierce the aerosol source member, including for example, a substantially cylindrical shape, a substantially prismatic shape, a substantially cuboidal shape, etc.

In various implementations, a heating member of the heating assembly 110 may generate heat upon receiving electrical energy from the electrical energy source 108. In such a manner, in some implementations the plurality of spikes 112 may comprise a resistive heating member that heats the substrate material 210 via contact with the substrate material 210. Because the plurality of spikes 112 extends into a portion of the interior area 208 of the substrate material 210, the substrate material 210 of the depicted implementation is heated from the inside outward. Direct contact may be preferred in light of the ability to provide conduction heating that is more rapid and that requires less thermal resistance. In various implementations, the plurality of spikes 112 may be constructed of a heat conducting material. For example, in some implementations the plurality of spikes 112 are chemically non-reactive with the materials comprising the substrate material being heated so as not to adversely affect the flavor or content of the aerosol or vapor that is produced. As noted above, example, non-limiting, materials that may comprise the plurality of spikes 112 include carbon, graphite, carbon/graphite composites, metallic and non-metallic carbides, nitrides, silicides, intermetallic compounds, cermets, and metal alloys. In some implementations, metal foils may be used.

In some implementations, additional heating members may be used. For example, some additional heating members may have other shapes that correspond to the shape of the substrate material in the aerosol source member. Other examples of heater arrays that could be adapted for use in the present disclosure per the discussion provided above can be found in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.;

U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., which are incorporated herein by reference in their entireties.

FIG. 3 illustrates a perspective schematic view of a heated end 302 of an aerosol source member and a portion of a heating assembly, according to another example implementation of the present disclosure. In particular, the heated end 302 of the aerosol source member defines an outer surface 306 and an interior area 308. In the depicted implementation, a substrate material 310 is located in the interior area 308 of the heated end 302 of the aerosol source member. As noted above, in some implementations, substrate material may be located in both the heated end 302 and the mouth end of the aerosol source member. In the depicted implementation, the substrate material 310 has a single segment, although in other implementations the substrate material 310 may include additional segments, which may have different compositions. In various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Reference is made to the possible substrate materials, compositions, components, and/or additives for use in a substrate material (and/or multiple substrate materials) above.

As described above, heating of the substrate material 310 results in aerosolization of the aerosol precursor composition associated with the substrate material 310. In various implementations, the mouth end of the aerosol source member is configured to receive the generated aerosol therethrough in response to a draw applied to the mouth end by a user. In some implementations, the mouth end of the aerosol source member may include a filter configured to receive the aerosol therethrough in response to the draw applied to the mouth end of the aerosol source member. Preferably, the elements of the substrate material 310 do not experience thermal decomposition (e.g., charring, scorching, or burning) to any significant degree, and the aerosolized components are entrained in the air that is drawn through the aerosol delivery device 100, including a filter (if present), and into the mouth of the user.

As shown in FIG. 3, the heating assembly of the depicted implementation includes a plurality of spikes 112 that are configured to articulate between a retracted position, in which the spikes are not in contact with aerosol source member, and a heating position, in which spikes contact the aerosol source member. In particular, FIG. 3 shows the spikes 112 in a heating position. In various implementations of the heating position, the spikes 112 not only contact the aerosol source member but also pierce through the outer surface 306 of the aerosol source member such that a portion of the spikes 112 extends into the substrate material 310. In various implementations, the degree to which the spikes 112 extend into the substrate material may vary. For example, in some implementations the spikes 112 may extend into the substrate material a small degree, while in other implementations the spikes 112 may extend to the center of the substrate material 310, and in still other implementations, the spikes 112 may extend through the center of the substrate material 310.

In various implementations, the plurality of spikes 112 may comprise opposing rows of spikes 112, such as those illustrated in FIG. 3, with one row being positioned on one side of the aerosol source member, and the other row being positioned on an opposite side of the aerosol source member. It should be noted that in some implementations, there may be additional rows of spikes 112, such as, for example, three or more rows that may be positioned around a circumference of the heated end 302 of the aerosol source member. In other implementations, however, there may be a single row of spikes 112. In some implementations, the positioning of the individual spikes 112 may be staggered between the rows, such as those illustrated in FIG. 3, while in other implementations the positioning of the individual spikes 112 may be substantially aligned. As noted above, in various implementations articulation of the plurality of spikes 112 may occur in different ways. For example, in some implementations the plurality of spikes 112 may be contained in a clamshell housing that moves away from the aerosol source member in the retracted position and toward the aerosol source member in the heating position. In some implementations, activation of the articulating motion may be triggered by a button. For example, in some implementations the clamshell housing may be spring-loaded, and a button may trigger the clamshell housing to move from the retracted position to the heating position. In another implementation, a user may slide a feature that carries one or both of the rows spikes 112 from the retracted position to the heating position, in which the spikes 112 pierce through the outer surface of the substrate material and into a portion of the interior area 308 thereof.

In various implementations, a heating member of the heating assembly may generate heat upon receiving electrical energy from the electrical energy source. In such a manner, in some implementations the plurality of spikes 112 may comprise a resistive heating member that heats the substrate material 310 via a supplemental heat conducting material in addition to contact with the substrate material 310. In the depicted implementation, the supplemental heat conducting material comprises a plurality of spaced conductive bands 320. In such a manner, in addition to, or as an alternative to, heating of the substrate material 310 via the spikes 112 themselves, the substrate material 310 may be heated by the plurality of spaced conductive bands 320 via heat conduction from the plurality of spikes 112. In some implementations, the plurality of conductive bands 320 may be constructed of a metal material, such as, but not limited to, copper, aluminum, platinum, gold, silver, iron, steel, brass, bronze, or any combination thereof. In other implementations, the plurality of conductive bands 320 may be constructed of a coated metal, such as, for example, aluminum-coated copper or other combinations of coatings and base materials chosen from the list above. In still other implementations, the plurality of conductive bands 320 may be constructed of a ceramic material, such as, but not limited to, aluminum oxide, beryllium oxide, boron nitride, silicon carbide, silicon nitride, aluminum nitride, or any combination thereof. In still other implementations, the plurality of conductive bands 320 may be constructed of a carbon material, such as, but not limited to, graphite, graphene, carbon nanotubes, nanoribbons, diamond-like structured carbon materials, or combinations thereof. In still other implementations, the plurality of conductive bands 320 may be constructed of polymer composites, such as polymer materials with metal, ceramic, or carbon fibers. For example, some implementations may comprise polyimide, epoxy, or silicone polymers, with boron nitride, zinc oxide, or alumina fibers. In further implementations, the present disclosure contemplates that the plurality of conductive bands 320 may be constructed of any one or any combination of the above materials, or composites that include two or more of the above materials.

FIG. 4 illustrates a perspective schematic view of a heated end 402 of an aerosol source member; FIG. 5 illustrates a perspective schematic view of the heated end 402 of the aerosol source member and a portion of a heating assembly; and FIG. 6 illustrates a top schematic view of the heated end of the aerosol source member and a portion of the heating assembly, according to other example implementations of the present disclosure. In the depicted implementation, the heated end 402 of the aerosol source member defines a first outer surface 406 and a first interior area 408, with a first substrate material 410 located in the first interior area 408 of the heated end 402 of the aerosol source member. As noted above, in some implementations, substrate material may be located in both the heated end 402 and the mouth end of the aerosol source member. In the depicted implementation, the first substrate material 410 has a single segment, although in other implementations the first substrate material 410 may include additional segments, which may have different compositions. In various implementations, the first substrate material 410 may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Reference is made to the possible substrate materials, compositions, components, and/or additives for use in a substrate material (and/or multiple substrate materials) above.

The depicted implementation also includes a second substrate material 412, which substantially surrounds the first substrate material 410. In particular, the second substrate material 412 of the depicted implementation is positioned proximate the first outer surface 406 of the first substrate material 410 and defines its own second outer surface 416 and second interior area 418. As with the first substrate material 410, in the depicted implementation the second substrate material 412 has a single segment, although in other implementations the second substrate material 412 may include additional segments, which may have different compositions. In various implementations, the second substrate material 412 may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Reference is made to the possible substrate materials, compositions, components, and/or additives for use in a substrate material (and/or multiple substrate materials) above. While in some implementations, the first substrate material 410 and the second substrate material 412 may comprise the same material, in various other implementations, the first substrate material 410 and the second substrate material 412 may comprise different materials. For example, in some implementations the first substrate material 410 and the second substrate material 412 may include one or more respective components that are desired to be kept separate. For example, in one implementation one of the substrate materials may include an ionized calcium (e.g., Ca++) component and the other substrate material may include an alginate component.

As described above, heating of the first substrate material 410 and/or the second substrate material 412 results in aerosolization of aerosol precursor composition(s) associated with the substrate materials 410, 412. In various implementations, the mouth end of the aerosol source member is configured to receive the generated aerosol therethrough in response to a draw applied to the mouth end by a user. In some implementations, the mouth end of the aerosol source member may include a filter configured to receive the aerosol therethrough in response to the draw applied to the mouth end of the aerosol source member. Preferably, the elements of the substrate materials 410, 412 do not experience thermal decomposition (e.g., charring, scorching, or burning) to any significant degree, and the aerosolized components are entrained in the air that is drawn through the aerosol delivery device 100, including a filter (if present), and into the mouth of the user.

As shown in FIGS. 5 and 6, the heating assembly of the depicted implementation includes a plurality of spikes 112 that are configured to articulate between a retracted position, in which the spikes 112 are not in contact with aerosol source member, and a heating position, in which spikes 112 contact the aerosol source member. In particular, FIGS. 5 and 6 show the spikes 112 in a heating position. In various implementations of the heating position, the spikes 112 not only contact the aerosol source member but also pierce through the second outer surface 416 of the aerosol source member such that a portion of the spikes 112 extends into the second substrate material 412. In some implementations, the spikes 112 extend only into the second substrate material 412 and not into the first substrate material 410. In such implementations, the distance to which the spikes 112 extend into the second substrate material 412 may vary. For example, in some implementations the spikes 112 may extend into the second substrate material 412 a short distance, while in other implementations the spikes 112 may extend to the center of the second substrate material 412, and in still other implementations, the spikes 112 may extend through the second substrate material 412. In the depicted implementation, the spikes 112 extend through the second substrate material 412 and further extend through the first outer surface 406 and into the first substrate material 410. In such implementations, the extent to which the spikes 112 extend into the first substrate material 410 may vary. For example, in some implementations the spikes 112 may extend into the first substrate material 410 a short distance, while in other implementations the spikes 112 may extend to the center of the first substrate material 410, and in still other implementations, the spikes 112 may extend through the center of the first substrate material 410.

In various implementations, the plurality of spikes 112 may comprise opposing rows of spikes 112, such as those illustrated in FIG. 5, with one row being positioned on one side of the aerosol source member, and the other row being positioned on an opposite side of the aerosol source member. It should be noted that in some implementations, there may be additional rows of spikes 112, such as, for example, three or more rows that may be positioned around a circumference of the heated end 402 of the aerosol source member. In other implementations, however, there may be a single row of spikes 112. In some implementations, the positioning of the individual spikes 112 may be staggered between the rows, such as those illustrated in FIG. 5, while in other implementations the positioning of the individual spikes 112 may be substantially aligned. As noted above, in various implementations articulation of the plurality of spikes 112 may occur in different ways. For example, in some implementations the plurality of spikes 112 may be contained in a clamshell housing that moves away from the aerosol source member in the retracted position and toward the aerosol source member in the heating position. In some implementations, activation of the articulating motion may be triggered by a button. For example, in some implementations the clamshell housing may be spring-loaded, and a button may trigger the clamshell housing to move from the retracted position to the heating position. In another implementation, a user may slide a feature that carries one or both of the rows spikes 112 from the retracted position to the heating position, in which the spikes 112 pierce through an outer surface of a substrate material and into a portion of an interior area 408 thereof.

As noted above, in various implementations a heating member of the heating assembly may generate heat upon receiving electrical energy from the electrical energy source. In such a manner, in some implementations the plurality of spikes 112 may comprise a resistive heating member that heats the first and second substrate materials 410, 412 via a supplemental heat conducting material in addition to contact with the substrate materials 410, 412 themselves. In the depicted implementation, the supplemental heat conducting material comprises a plurality of spaced conductive bands 420 that are located between the first outer surface 406 of the first substrate material 410 and an inner surface of the second substrate material 412. In such a manner, in addition to, or as an alternative to, heating of the first and second substrate materials 410, 412 via the spikes 112 themselves, the first and second substrate materials 410, 412 may be heated by the plurality of spaced conductive bands 420 via heat conduction from the plurality of spikes 112. In some implementations, the plurality of spaced conductive bands 420 may be constructed of a metal material, such as, but not limited to, copper, aluminum, platinum, gold, silver, iron, steel, brass, bronze, or any combination thereof. In other implementations, the plurality of conductive bands 420 may be constructed of a coated metal, such as, for example, aluminum-coated copper or other combinations of coatings and base materials chosen from the list above. In still other implementations, the plurality of spaced conductive bands 420 may be constructed of a ceramic material, such as, but not limited to, aluminum oxide, beryllium oxide, boron nitride, silicon carbide, silicon nitride, aluminum nitride, or any combination thereof. In still other implementations, the plurality of heat conductive bands 420 may be constructed of a carbon material, such as, but not limited to, graphite, graphene, carbon nanotubes, nanoribbons, diamond-like structured carbon materials, or combinations thereof. And in still other implementations, the plurality of heat conductive bands 420 may be constructed of polymer composites, such as polymer materials with metal, ceramic, or carbon fibers, including, but not limited to, polyimide, epoxy, or silicone polymers, with boron nitride, zinc oxide, or alumina fibers. In further implementations, the present disclosure contemplates that the plurality of conductive bands may be constructed of any one or any combination of the above materials, or composites that include two or more of the above materials.

It should be noted that while in in the depicted implementations substrate material resides under the conductive bands as well as between the conductive bands, in other implementations, aerosol source material may reside solely under the conductive bands, or, in other implementations, solely between the conductive bands. In addition, while ion the depicted implementations the concentration of the aerosol generating material in the substrate material is relatively consistent throughout the segments, in some implementations, the concentration of the aerosol generating materials in the substrate material may vary from segment to segment.

FIG. 7 illustrates a perspective schematic drawing of a portion of a heated end 502 of an aerosol source member and a portion of a heating assembly, and FIG. 8 illustrates a top schematic view of the heated end 502 of the aerosol source member and a portion of the heating assembly, according to an example implementation of the present disclosure. In particular, the heated end 502 of the aerosol source member defines a first outer surface 506 and a first interior area 508, with a first substrate material 510 located in the first interior area 508 of the heated end 502 of the aerosol source member. As noted above, in some implementations, substrate material may be located in both the heated end 502 and the mouth end of the aerosol source member. In the depicted implementation, the first substrate material 510 has a single segment, although in other implementations the first substrate material 510 may include additional segments, which may have different compositions. In various implementations, the first substrate material 510 may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Reference is made to the possible substrate materials, compositions, components, and/or additives for use in a substrate material (and/or multiple substrate materials) above.

The depicted implementation also includes a second substrate material 512, which substantially surrounds the first substrate material 510. In particular, the second substrate material 512 of the depicted implementation is positioned proximate the first outer surface 506 of the first substrate material 510 and defines its own second outer surface 516 and second interior area 518. As with the first substrate material 510, in the depicted implementation the second substrate material 512 has a single segment, although in other implementations the second substrate material 510 may include additional segments, which may have different compositions. In various implementations, the second substrate material 512 may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Reference is made to the possible substrate materials, compositions, components, and/or additives for use in a substrate material (and/or multiple substrate materials) above. While in some implementations, the first substrate material 510 and the second substrate material 512 may comprise the same material, in various other implementations, the first substrate material 510 and the second substrate material 512 may comprise different materials. For example, in some implementations the first substrate material 510 and the second substrate material 512 may include one or more respective components that are desired to be kept separate. For example, in one implementation one of the substrate materials may include an ionized calcium (e.g., $Ca^{++}$) component and the other substrate material may include an alginate component.

As described above, heating of the first substrate material 510 and/or the second substrate material 512 results in aerosolization of aerosol precursor composition(s) associated with the substrate materials 510, 512. In various implementations, the mouth end of the aerosol source member is configured to receive the generated aerosol therethrough in response to a draw applied to the mouth end by a user. In some implementations, the mouth end of the aerosol source member may include a filter configured to receive the aerosol therethrough in response to the draw applied to the mouth end of the aerosol source member. Preferably, the elements of the substrate materials 510, 512 do not experience thermal decomposition (e.g., charring, scorching, or burning) to any significant degree, and the aerosolized components are entrained in the air that is drawn through the aerosol delivery device 100, including a filter (if present), and into the mouth of the user.

As shown in FIGS. 7 and 8, the heating assembly of the depicted implementation includes a plurality of spikes 112 that are configured to articulate between a retracted position, in which the spikes 112 are not in contact with aerosol source member, and a heating position, in which spikes 112 contact a plurality of spaced conductive bands 520 that extend around a limited portion of the outer surface of the first substrate material 510. In particular, FIGS. 7 and 8 show the spikes 112 in a heating position. In the depicted implementation, the plurality of spaced conductive bands 520 serves as the heating member. In particular, each of the plurality of spaced conductive bands 520 of the depicted implementation defines a first end 520*a* and a second end 520*b*. In such a manner, when the plurality of spikes 112, which are electrically connected to an electrical energy source 108, contacts respective first and second ends 520*a*, 520*b* of the plurality of spaced conductive bands 520, a plurality of resistive heating circuits are completed such that the plurality of spaced conductive bands 520 serves as the heating member.

In some implementations, the plurality of spaced conductive bands 520 may be constructed of a metal material, such as, but not limited to, copper, aluminum, platinum, gold, silver, iron, steel, brass, bronze, or any combination thereof. In other implementations, the plurality of conductive bands 520 may be constructed of a coated metal, such as, for example, aluminum-coated copper or other combinations of coatings and base materials chosen from the list above. In still other implementations, the plurality of spaced conductive bands 520 may be constructed of a ceramic material, such as, but not limited to, aluminum oxide, beryllium oxide, boron nitride, silicon carbide, silicon nitride, aluminum nitride, or any combination thereof. In still other implementations, the plurality of heat conductive bands 520 may be constructed of a carbon material, such as, but not limited to, graphite, graphene, carbon nanotubes, nanoribbons, diamond-like structured carbon materials, or combinations thereof. And in still other implementations, the plurality of heat conductive bands 520 may be constructed of polymer composites, such as polymer materials with metal, ceramic, or carbon fibers, including, but not limited to, polyimide, epoxy, or silicone polymers, with boron nitride, zinc oxide, or alumina fibers. In further implementations, the present disclosure contemplates that the plurality of conductive bands may be constructed of any one or any combination of the above materials, or composites that include two or more of the above materials.

In some implementations of the heating position, the spikes 112 not only contact the aerosol source member but also pierce through the second outer surface 516 of the aerosol source member such that a portion of the spikes 112 extends into the second substrate material 512. In some implementations, the spikes 112 extend only into the second substrate material 512 and not into the first substrate material 510. In such implementations, the distance to which the spikes 112 extend into the second substrate material 512 may vary. For example, in some implementations the spikes 112 may extend into the second substrate material 512 a short distance, while in other implementations the spikes 112 may extend to the center of the second substrate material 512, and in still other implementations, the spikes 112 may extend through the second substrate material 512. For example, in the depicted implementation the spikes 112 extend through the second substrate material 512 and further extend through the first outer surface 506 and into the first substrate material 510. In such implementations, the extent to which the spikes 112 extend into the first substrate material 510 may vary. For example, in some implementations the spikes 112 may extend into the first substrate material 510 a short distance, while in other implementations the spikes 112 may extend to the center of the first substrate material 510, and in still other implementations, the spikes 112 may extend through the center of the first substrate material 510.

In various implementations, the plurality of spikes 112 may comprise a pair of rows of spikes 112, such as those illustrated in FIG. 7, with one row being positioned proximate the other row on the same side of the aerosol source member. In the depicted implementation, the rows of spikes 112 are substantially aligned; however, in other implementations, such as, for example, an implementation in which the spaced conductive bands have a spiral pattern around the substrate material, the rows of spikes may be staggered. It should be noted, however, that for any of the implementations discussed herein the plurality of spikes need not be arranged in a pattern, and thus, in some implementations, the plurality of spikes may be distributed randomly. As noted above, in various implementations articulation of the plurality of spikes 112 may occur in different ways. For example, in some implementations the plurality of spikes 112 may be contained in a clamshell housing that moves away from the aerosol source member in the retracted position and toward the aerosol source member in the heating position. In some implementations, activation of the articulating motion may be triggered by a button. For example, in some implementations the clamshell housing may be spring-loaded, and a button may trigger the clamshell housing to move from the retracted position to the heating position. In another implementation, a user may slide a feature that carries one or both of the rows spikes from the retracted position to the heating position, in which the heat conducting spikes 112 pierce through an outer surface of a substrate material and into a portion of an interior area 508 thereof.

For any of the implementations described above, the control component 106 and/or the plurality of spikes 112 may be configured such that substrate material (e.g., a first substrate material or first and second substrate materials) may be heated in segments. In such a manner, the plurality of spikes 112 may be configured to be independently controllable. For example, in some implementations individual spikes 112, pairs of spikes 112, and/or groups of spikes 112 may be independently controllable such that various portions of the substrate material may be heated at different times. In one implementation, individual spikes 112, pairs of spikes 112, and/or groups of spikes 112 may be independently activated (e.g., independently articulated and/or independently heated and/or independently connected to an electrical energy source) so that the substrate material is sequentially heated. This could occur via heating from the spikes and/or the conductive bands, as described above. In such implementations, activation of the spikes 112 may be initiated by the puffing action of the consumer through the use of one or more various sensors, as otherwise described herein, and/or may be initiated once the puff is discontinued as sensed by one or more various sensors, such as a button.

Thus, in some implementations, a number of possible heating segments may correspond to a number of puffs available from the aerosol source member 200. In some implementations, a single aerosol source member may provide about 4 to about 12, about 5 to about 11, or about 6 to about 10 puffs, It should be noted that although the aerosol source member and control body of the present disclosure may be provided together as a complete smoking article or pharmaceutical delivery article generally, the components also may be provided separately. For example, the present disclosure also encompasses a disposable unit for use with a reusable smoking article or a reusable pharmaceutical delivery article. In specific implementations, such a disposable unit (which may be an aerosol source member as illustrated in the appended figures) can comprise a substantially tubular shaped body having a heated end configured to engage the reusable smoking article or pharmaceutical delivery article, an opposing mouth end configured to allow passage of an inhalable substance to a consumer, and a wall with an outer surface and an inner surface that defines an interior space. Various implementations of an aerosol source member (or cartridge) are described in U.S. Pat. No. 9,078,473 to Worm et al., which is incorporated herein by reference.

In addition to the disposable unit, the present disclosure may further be characterized as providing a separate control body for use in a reusable smoking article or a reusable pharmaceutical delivery article. In specific implementations, the control body may generally be a housing having a receiving end (which may include a receiving chamber with an open end) for receiving a heated end of a separately provided aerosol source member. The control body may further include an electrical energy source that provides power to an electrical heating member, which may be a component of the control body or may be included in aerosol source member to be used with the control unit. In various implementations, the control body may also include further components, including an electrical power source (such as a battery), components for actuating current flow into the heating member, and components for regulating such current flow to maintain a desired temperature for a desired time and/or to cycle current flow or stop current flow when a desired temperature has been reached or the heating member has been heating for a desired length of time. In some implementations, the control unit further may comprise one or more pushbuttons associated with one or both of the components for actuating current flow into the heating member, and the components for regulating such current flow. The control body may also include one or more indicators, such as lights indicating the heater is heating and/or indicating the number of puffs remaining for an aerosol source member that is used with the control body.

Although the various figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

an aerosol source member that defines an outer surface and an interior area and includes a substrate material having an aerosol precursor composition associated therewith;

a control body having a housing that is configured to receive the aerosol source member;

an electrical energy source coupled with the housing; and a plurality of spikes comprising a heating assembly connected to the electrical energy source, the plurality of spikes extending along a longitudinal axis parallel to the aerosol source member, wherein the plurality of spikes are configured to articulate between a retracted position, in which the plurality of spikes are not in contact with the aerosol source member, and a heating position, in which the plurality of spikes pierce through the outer surface of the substrate material and into a portion of the interior area thereof.

2. The aerosol delivery device of claim 1, wherein the outer surface of the substrate material includes a plurality of spaced conductive bands.

3. The aerosol delivery device of claim 2, wherein each of the spaced conductive bands circumscribes the entire outer surface of the substrate material.

4. The aerosol delivery device of claim 2, wherein each of the spaced conductive bands extends around a limited portion of the outer surface of the substrate material and defines a first end and a second end.

5. The aerosol delivery device of claim 4, wherein in the heating position, respective spikes of the plurality of heat conducting spikes contact the first and second ends of the spaced conductive bands.

6. The aerosol delivery device of claim 5, wherein the plurality of spaced conductive bands comprises a heating member of the heating assembly.

7. The aerosol delivery device of claim 1, wherein the plurality of spikes comprises a heating member of the heating assembly.

8. The aerosol delivery device of claim 1, wherein the aerosol source member further comprises a second substrate material that defines an outer surface and an interior area, and wherein the second substrate material surrounds the first substrate material.

9. The aerosol delivery device of claim 8, wherein the outer surface of the first substrate material includes a plurality of spaced conductive bands.

10. The aerosol delivery device of claim 9, wherein each of the spaced conductive bands circumscribes the entire outer surface of the substrate material.

11. The aerosol delivery device of claim 9, wherein each of the spaced conductive bands extends around a portion of the outer surface of the substrate material and defines a first end and a second end.

12. The aerosol delivery device of claim 11, wherein in the heating position, respective spikes of the plurality of spikes contact the first and second ends of the spaced conductive bands.

13. The aerosol delivery device of claim 12, wherein the plurality of spaced conductive bands comprises a heating member of the heating assembly.

14. The aerosol delivery device of claim 9, wherein the plurality of spikes comprises a heating member of the heating assembly.

15. The aerosol delivery device of claim 8, wherein the first substrate material comprises a first composition, wherein the second substrate material comprises a second composition, and wherein the first composition is different than the second composition.

16. The aerosol delivery device of claim 8, wherein the first substrate material comprises at least one of shreds of tobacco material, beads of tobacco material, an extruded structure of tobacco material, a crimped sheet of tobacco material, and combinations thereof.

17. The aerosol delivery device of claim 8, wherein the second substrate material comprises at least one of shreds of tobacco material, beads of tobacco material, an extruded structure of tobacco material, a crimped sheet of tobacco material, and combinations thereof.

18. The aerosol delivery device of claim 1, wherein the substrate material comprises at least one of a tobacco material and a tobacco-derived material.

19. The aerosol delivery device of claim 1, wherein the substrate material comprises a non-tobacco material.

20. The aerosol delivery device of claim 1, wherein the substrate material comprises at least one of shreds of tobacco material, beads of tobacco material, an extruded structure of tobacco material, a crimped sheet of tobacco material, and combinations thereof.

* * * * *